United States Patent [19]

Öhlschläger et al.

[11] Patent Number: 4,579,816
[45] Date of Patent: Apr. 1, 1986

[54] YELLOW DIR COUPLER WITH 5-FURYL(1,2,4-TRIAZOLE) COUPLING OFF GROUP

[75] Inventors: Hans Öhlschläger, Bergisch Gladbach; Ulrich Griesel; Heinrich Odenwälder, both of Leverkusen, all of Fed. Rep. of Germany

[73] Assignee: Agfa-Gevaert Aktiengesellschaft, Leverkusen, Fed. Rep. of Germany

[21] Appl. No.: 754,652

[22] Filed: Jul. 15, 1985

[30] Foreign Application Priority Data

Jul. 24, 1984 [DE] Fed. Rep. of Germany ....... 3427235

[51] Int. Cl.⁴ ............................ G03C 1/40; G03C 7/36
[52] U.S. Cl. .................................. 430/544; 430/557; 430/558; 430/957
[58] Field of Search ........................ 430/544, 557, 957

[56] References Cited

U.S. PATENT DOCUMENTS 4,182,630  1/1980  Quaglia ................................ 430/558
4,359,521  11/1982  Fryberg et al. ..................... 430/544

Primary Examiner—Richard L. Schilling
Attorney, Agent, or Firm—Connolly & Hutz

[57] ABSTRACT

Yellow DIR couplers corresponding to formula I below are capable of producing remarkably powerful inhibitory effects on remote layers while their action on the layer containing them is comparatively slight:

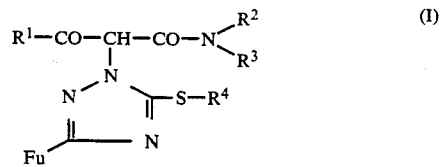

In the above formula,
$R^1$ represents straight-chained or branched alkyl, optionally substituted aryl or $-NR^5R^6$,
$R^2$, $R^5$ represent H or alkyl with 1 or 2 carbon atoms,
$R^3$, $R^6$ represent alkyl with 1 to 18 carbon atoms or optionally substituted aryl,
$R^4$ represents alkyl with 5 to 12 carbon atoms, and
Fu represents a substituted or unsubstituted furyl group.

3 Claims, No Drawings

YELLOW DIR COUPLER WITH 5-FURYL(1,2,4-TRIAZOLE) COUPLING OFF GROUP

This invention relates to a colour photographic recording material having at least one light-sensitive silver halide emulsion layer containing a yellow coupler which releases a development inhibitor in the course of colour development.

It is known that chromogenic development may be carried out in the presence of compounds which, in the course of development, release diffusible substances in imagewise distribution, which substances are capable of inhibiting the development of silver halide. Such compounds are known as so-called DIR compounds (DIR=development inhibitor releasing). The DIR compounds may be of the kind which split off an inhibitor group and react with the oxidation product of a colour developer to produce a dye (DIR coupler) or they may release the inhibitor without at the same time forming a dye. Compounds of the the last mentioned type are also referred to as DIR compounds in the strict sense.

DIR couplers have been disclosed, for example, in U.S. Pat. Nos. 3,148,062, 3,227,554, 3,615,506 and 3,617,291.

The development inhibitors released are in most cases heterocyclic mercapto compounds or derivatives of benzotriazole. Information on those DIR compounds which undergo coupling to form mainly colourless products may be found, for example, in U.S. Pat. No. 3,632,345, DE-A Nos. 2 359 295 and DE-A 2 540 959. Numerous photographic effects which influence the quality of the image can be obtained by using DIR compounds. These effects include, for example, a reduction in gradation, a finer colour grain, an improvement in the sharpness due to the so-called edge effect and an improvement in the purity and brilliance of the colour due to so-called interimage effects. See, for example, the publication entitled "Development-Inhibitor-Releasing (DIR) Couplers in Color Photography" by C. R. Barr, J. R. Thirtle and P. W. Vittum, Photographic Science and Engineering 13, 74 (1969).

DIR compounds, which undergo colourless coupling, have the advantage over DIR couplers, which undergo coupling to produce coloured compounds, that they are universally applicable so that one and the same compound may be used in all the light-sensitive layers of a colour photographic recording material without regard to the colour to be produced. DIR couplers, on the other hand, have the disadvantage, due to the colour produced from them, that they usually can only be used in some of the light-sensitive layers if the colour side density caused by them in the other layers is not acceptable. Against this advantage of DIR compounds, however, is the disadvantage that they are generally less reactive than DIR couplers. Photographic practice has therefore in most cases been restricted to the use of DIR couplers, and, if necessary, two or more different DIR couplers have been used in the same recording material, layers with different spectral sensitivities having been associated with different DIR couplers according to the colour to be produced from the couplers.

DE-A No. 2 842 063 discloses DIR couplers which are derived from yellow couplers and contain a 3-alkylthio-1,2,4-triazolyl group as the releasable inhibitor group.

When the DIR couplers described in the above mentioned document are used in a blue-sensitive silver halide emulsion layer, the colour gradation in this layer may be considerably reduced but the effect on adjacent silver halide layers, in particular an adjacent greensensitive and/or red-sensitive silver halide emulsion layer, is comparatively slight. The known DIR couplers are therefore only capable of producing slight interimage effects.

It is an object of the present invention to provide a colour photographic recording material containing yellow DIR couplers which are capable of producing comparatively powerful interimage effects.

The invention relates to a colour photographic recording material having at least one light-sensitive silver halide emulsion layer and, associated with this layer, a DIR coupler which carries a releasable 1,2,4-triazolyl group attached to a yellow coupler at the coupling position, characterised in that the DIR coupler corresponds to the following formula (I):

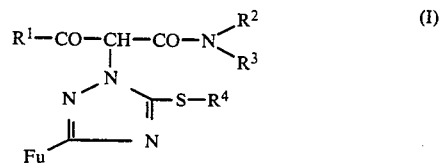

wherein
$R^1$ represents a straight-chained or branched alkyl group, an optionally substituted aryl group or $-NR^5R^6$,
$R^2$, $R^5$ represent H or alkyl with 1 to 3 carbon atoms,
$R^3$, $R^6$ represent alkyl with 1 to 18 carbon atoms or optionally substituted aryl,
$R^4$ represents alkyl with 5 to 12 carbon atoms, and
Fu represents an optionally substituted furyl group.

An alkyl group represented by $R^1$ contains 1 to 18 carbon atoms. It may be straight-chained or branched and is preferably a tertiary alkyl group. The following are examples: methyl, ethyl, propyl, isopropyl, n-butyl, t-butyl, t-amyl, and 1,1,3,3-tetramethyl-butyl. The alkyl group may also be a cyclic or bicyclic group, such as a norbornyl or adamantyl group.

The aryl group represented by $R^1$ or $R^3$ may be, in particular, a phenyl group which may be substituted, e.g. by alkyl, alkoxy, halogen, carbamoyl, sulphamoyl or acylamino. The acyl group may be derived from aliphatic or aromatic carboxylic acids or from sulphonic acids or carbonic acid monoesters or carbamic acids.

An alkyl group represented by $R^4$ may be straight-chained or branched and may be substituted by aryl (e.g. benzyl).

The symbol Fu represents a furyl group which is attached via the 2- or 3-position and may contain further substituents, e.g. furyl-2, 2-methylfuryl-3, or 5-nitrofuryl-2.

According to formula (I), the 1,2,4-triazole ring is attached by one of its two adjacent ring nitrogen atoms to the coupling position of the yellow coupler. Since, however, it has to this day not been completely clarified whether this corresponds to the true facts, formula (I) is intended also to represent the corresponding isomers in which the 1,2,4-trazole ring may be attached to the coupling position through any other ring nitrogen atom.

Examples of suitable yellow DIR couplers according to the present invention are shown in Table 1 ($R^2$=H; Fu=2-furyl).

TABLE 1

| Compound | $R^1$ | $R^3$ | $R^4$ |
|---|---|---|---|
| 1 | t-$C_4H_9$— | Cl | —n-$C_6H_{13}$ |
| | | 3-methylphenyl-NH-CO-(CH$_2$)$_3$-O-[2,4-bis(t-$C_5H_{11}$)phenyl] | |
| 2 | " | " | —n-$C_8H_{17}$ |
| 3 | " | " | —$CH_2$—phenyl |
| 4 | $CH_3$—O—(4-phenyl)— | 4-$OC_{16}H_{33}$-3-methyl-phenyl-$SO_2$—NH—$CH_3$ | —n-$C_6H_{13}$ |
| 5 | $CH_3$—O—phenyl— | phenyl-$SO_2$—NH—$CH_3$ | —($CH_2$)$_2$—CH($CH_3$)—$CH_2$—C($CH_3$)$_3$ |
| 6 | 2-$OC_{14}H_{29}$-phenyl- | 4-$OCH_3$-3-methyl-phenyl-$SO_2$NH—$CH_3$ | —n-$C_6H_{13}$ |
| 7 | $C_{16}H_{33}$—O—(4-phenyl)— | 4-$OCH_3$-3-methyl-phenyl-$SO_2$—N($CH_3$)$_2$ | —n-$C_6H_{13}$ |
| 8 | " | " | —n-$C_{10}H_{21}$ |
| 9 | $CH_3O$—(4-phenyl)— | Cl, 3-methyl-4-[NH-CO-(CH$_2$)$_3$-O-(2,4-bis(t-$C_5H_{11}$)phenyl)]phenyl | —n-$C_6H_{13}$ |
| 10 | $CH_3$—O—($CH_2$)$_2$—O—(4-phenyl)— | 3-O-$C_2H_5$-4-methyl-phenyl-$SO_2$—N($CH_3$)($C_{18}H_{37}$) | —n-$C_6H_{13}$ |

TABLE 1-continued

| Compound | R¹ | R³ | R⁴ |
|---|---|---|---|
| 11 | 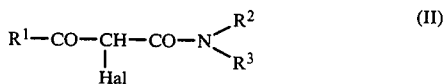 | 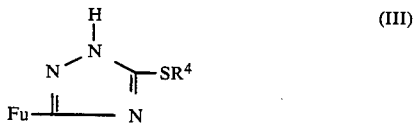 | —n-C₆H₁₃ |

The DIR couplers according to the invention corresponding to formula I may be readily obtained by condensation of the known α-halogenoacyl acetanilides corresponding to formula (II):

$$R^1-CO-CH(Hal)-CO-N\begin{smallmatrix}R^2\\R^3\end{smallmatrix} \quad (II)$$

wherein R¹ to R³ have the meanings already indicated and Hal represents a halogen atom, in particular chlorine or bromine, with triazoles corresponding to formula (III):

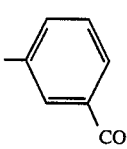

wherein R⁴ and Fu have the meanings indicated. The reaction is advantageously carried out in an organic solvent such as dimethylformamide, acetonitrile or acetone in the presence of a base such as triethylamine or caustic potash.

Triazoles corresponding to formula (III) may be obtained by reaction of the corresponding 3-mercapto-1,2,4-triazoles with suitable alkyl or aralkyl halides.

Since the triazoles of formula (III) may occur in various tautomeric forms and different mesomeric boundary structures may therefore be ascribed to the corresponding azeniate ion, the linkage with the carbon atom of the coupling position in the condensation reaction could conceivably take place by way of any of the ring nitrogen atoms present, which would explain the occurrance of the corresponding isomers. This isomerism, however, has no influence on the useful properties of the DIR couplers according to the invention and a detailed discussion of the structure of the possible isomers is therefore unnecessary.

The process of preparation of the DIR couplers according to the invention is described in more detail below with reference to the example of DIR coupler compound 4.

Compound 4 a. 3-Hexylthio-5-(furyl-2)-1,2,4-triazole 500 g of 3-mercapto-5-(furyl-2)-1,2,4-triazole, 530 g of hexyl bromide and 168 g of caustic potash were heated under reflux in 3000 ml of methanol for 8 hours. The KBr which precipitated in the course of the reaction was suction-filtered, about 2500 ml of methanol were distilled off, and the residue was stirred up with water. The product which precipitated was suction-filtered and dried.

Yield: 722 g.

Melting point 96° C. (after recrystallisation from cyclohexane).

b. Compound 4

356 g of α-(4-methoxybenzoyl)-α-chloro-2-hexadecyloxy-5-N-methylsulphamoylacetanilide and 140 g of the triazole prepared according to a) were stirred up with 63 g of caustic potash in 1500 ml of acetonitrile for 15 hours at room temperature. The reaction solution was poured out into 1500 ml of 10% hydrochloric acid and the oily product thus obtained was taken up in 500 ml of toluene. The solution in toluene was concentrated by evaporation and the oily residue was poured into 1300 ml of cyclohexane. The product which crystallised from the cyclohexane was suction-filtered and dried in air.

Yield: 300 g.

Melting point: 63°–65° C.

The compounds according to the present invention are suitable for use as yellow DIR couplers in colour photographic, particularly in multilayered recording materials. As yellow couplers, they are preferably used in or associated with a light-sensitive silver halide emulsion layer which has a predominant sensitivity for the blue spectral region of visible light. The special advantage of the yellow DIR couplers according to the invention, namely their comparatively slight inhibitory effect on development in the layer with which they are associated together with their comparatively powerful inhibitory action on development in adjacent layers with which they are not associated, is, of course, particularly important in a multilayered colour photographic recording material which, in addition to containing a predominantly blue-sensitive silver halide emulsion layer, contains other light-sensitive silver halide emulsion layers which are predominantly sensitive to the green or red spectral region of visible light. Technically advanced colour photographic recording materials contain at least one light-sensitive silver halide emulsion layer unit with associated colour couplers for each of the three spectral regions, blue, green and red. Each of these silver halide emulsion layer units may consist of one or more than one silver halide emulsion partial layer, and where several such partial layers are provided they are generally sensitized to the same region of the spectrum but may differ in their general sensitivity, the nature of the silver halide used, the nature of the colour coupler used, the proportion of coupler to silver and possibly also other physical or chemical parameters. The individual partial layers having the same spectral sensitivity may be spatially conbined to form silver halide layer units or they may be arranged so that a (partial) layer which is sensitive to one part of the visible spectrum is situated between two partial layers of a layer unit having a different spectral sensitivity. An intermediate or separating layer which is not sensitive to light is advantageously provided between two layers which differ in their spectral sensitivity.

As already mentioned above, at least one colour coupler is associated with each individual silver halide emulsion layer unit. The term "associated" means that the silver halide emulsion layer unit and the colour coupler are arranged in such a relationship to each other that, when development takes place, interaction between them is possible to produce an imagewise correspondence between the resulting silver image and the resulting colour image. For this purpose, the colour coupler may be incorporated in one or more of the silver halide emulsion partial layers of a silver halide emulsion layer unit or in a light-insensitive binder layer adjacent thereto.

The colour couplers which may be associated with two or more partial layers of a silver halide emulsion layer unit need not necessarily be identical, provided only that they give rise to the same colour in the process of colour development, normally a colour which is complementary to the colour of light to which the light-sensitive silver halide emulsion layers have the predominant sensitivity. The red-sensitive silver halide emulsion layers therefore have at least one colour coupler for producing the cyan partial colour image associated with them, generally a coupler of the phenol or α-naphthol series. Associated with the green-sensitive silver halide emulsion layers is at least one colour coupler for producing the magneta partial colour image, these colour couplers being normally of the 5-pyrazolone or the indazolone series. Associated with the blue-sensitive silver halide emulsion layers is at least one colour coupler for producing the yellow partial colour image, generally a colour coupler having an open-chain ketomethylene group. Colour couplers of these kinds are known in large numbers and have been described in numerous Patent Specifications. Reference may be made, for example, to the publications, "Farbkuppler" by W. Pelz in "Mitteilungen aus den Forschungslaboratorien der Agfa, Leverkusen/München", Volume III, page 111 (1961) and K.VENKATARAMAN in "The Chemistry of Synthetic Dyes", Vol. 4, 341 to 387, Academic Press (1971).

The colour couplers may be either conventional 4-equivalent couplers or they may be 2-equivalent couplers, which require a smaller quantity of silver halide for producing the colour. As is known, 2-equivalent couplers differ from 4-equivalent couplers in that they carry, in the coupling position, a substituent which is split off in the process of coupling. 2-Equivalent couplers suitable for the purpose of the present invention include both those which are virtually colourless and those which have an intense colour of their own which disappears in the process of colour coupling or is replaced by the colour of the image dye produced. According to the invention, the latter couplers may be present additionally in the light-sensitive silver halide emulsion layers and serve there as masking couplers to compensate for the unwanted side densities of the image dyes. Also to be included among the 2-equivalent couplers are the known white couplers which do not give rise to a dye in their reaction with colour developer oxidation products, as well as the known DIR couplers which are couplers containing, in the coupling position, a group which can be split off to be released as a diffusible development inhibitor in the reaction with colour developer oxidation products. This category of 2-equivalent couplers also includes the yellow DIR couplers of the present invention.

Mixtures of colour couplers may be used if required to obtain a particular colour shade or the desired reactivity. For example, water-soluble couplers may be used in combination with hydrophobic, water-insoluble couplers.

Both the colour couplers and the yellow DIR couplers according to the present invention are generally incorporated in a diffusion-fast form in their layer, although it may in some cases be advantageous to use colour couplers which have a certain, limited tendency to diffusion. The image dyes formed from the colour couplers in the process of development would generally be required to be no longer diffusible in the layers.

Although the invention has been described above with reference to recording materials in which the colour images are produced by chromogenic development using colour couplers, the invention is by no means restricted to such materials. The effect on the gradation of the layer in which the yellow DIR couplers according to the invention is contained as well as on the adjacent layers is completely independent of the nature of the other colour producing compounds used. Other types of colour producing compounds, such as developer dyes or dye-releasing compounds of the kind used in dye diffusion photographic processes may therefore be used in the same manner as the colour couplers mentioned above. One invariable precondition, however, is that development should be carried out under conditions which enable a diffusible development inhibitor, in this case a 3-alkylthio-5-furyl-1,2,4-triazole, to be released imagewise to the extent that an exposure has previously been carried out. This means that the colour photographic recording materials according to the present invention are developed in the presence of developer compounds whose oxidation products react with the yellow DIR couplers according to the invention to release a development inhibitor. Examples of suitable developer compounds of this kind include, for example, the conventionally used p-phenylenediamine compounds which carry a free primary amino group.

The quantity of yellow DIR couplers according to the invention to be used in the layer may vary within wide limits according to requirement, e.g. from $0.5 \cdot 10^{-4}$ to $50 \cdot 10^{-4}$ mol/m$^2$. Particularly suitable results are obtained, for example, with a quantity of yellow DIR couplers according to the invention in the range of from $1.0$ to $5.0 \cdot 10^{-4}$ mol/m$^2$. These couplers may be incorporated with the aid of conventional oil formers.

EXAMPLE

The invention is illustrated on the basis of the arrangement of layers described below. To prepare this arrangement, the layers indicated are applied in the sequence given to a transparent layer support of cellulose triacetate provided with an antihalation layer and an adhesive layer. The quantities given are based in each case on 1 m$^2$. The amount of silver applied is given in terms of the corresponding quantities of AgNO$_3$.

1. A less sensitive red-sensitive layer containing a red-sensitized silver iodobromide emulsion (5 mol-% AgI) of 3.5 g of AgNO$_3$ with 600 mg of a cyan coupler corresponding to the formula

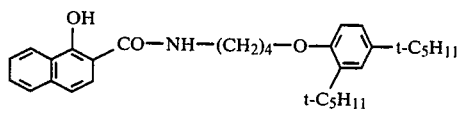

30 mg of a DIR coupler corresponding to the formula

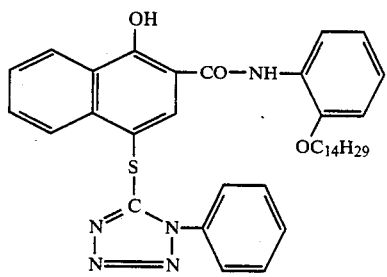

and 60 mg of a masking coupler corresponding to the formula

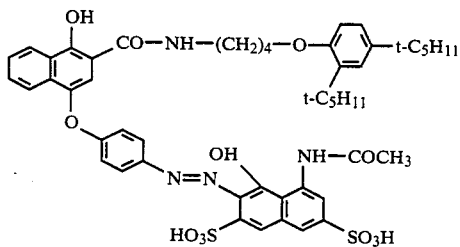

and 2.5 g of gelatine;

2. A more highly sensitive red-sensitive layer containing a red-sensitized silver iodobromide emulsion (8 mol-% AgI) of 3.0 g AgNO₃ with 200 mg of the cyan coupler of layer 1 and 2.7 g of gelatine;

3. An intermediate layer containing 0.8 g of gelatine and 0.1 g of 2,5-diisooctyl hydroquinone;

4. A less sensitive green-sensitive layer containing a green-sensitized silver iodobromide emulsion (6 mol-% AgI) of 2.5 g of AgNO₃ with 800 mg of magenta coupler corresponding to the formula

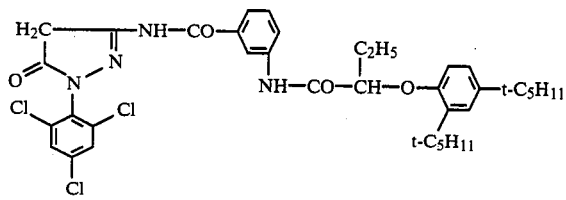

25 mg of a DIR coupler corresponding to the formula

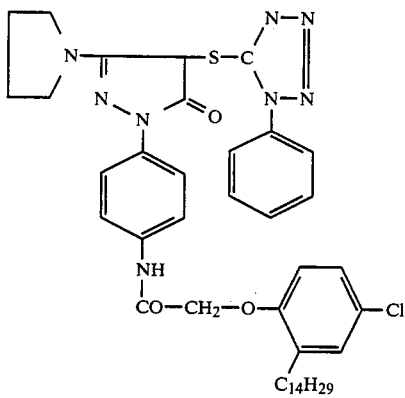

90 mg of a masking coupler of the formula

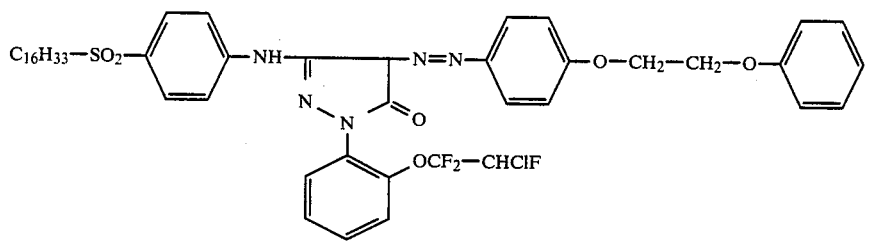

and 2.6 g of gelatine;

5. A more highly sensitive green-sensitive layer containing a green-sensitized silver iodobromide emulsion (10 mol-% AgI) of 2.0 g of AgNO₃ with 250 mg of the magneta coupler of layer 4 and 1.7 g of gelatine;

6. A yellow filter layer containing colloidal silver for producing a yellow density of 0.7, and 0.6 g of gelatine;

7. A less sensitive blue-sensitive layer containing a silver iodobromide emulsion (5 mol-% AgI) of 1.0 g of AgNO₃ with 700 mg of a yellow coupler corresponding to the formula

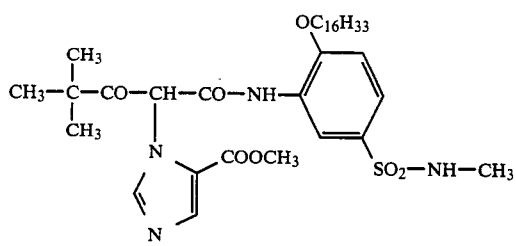

and a DIR coupler as indicated in Table 2 below, and 0.9 g of gelatine;

8. A more highly sensitive blue-sensitive layer containing a blue-sensitized silver iodobromide emulsion of 1.3 g of AgNO₃ with 300 mg of the yellow coupler of layer 7 and 0.7 g of gelatine; and 9. A covering layer containing 0.6 g of gelatine.

The couplers in layers 1, 2, 4, 5, 7 and 8 and the diisooctylhydroquinone in layer 3 are used in the form of an emulsion (1:1) with tricresylphosphate. The DIR couplers used in layer 7 and the inhibitory values obtained as a result in three partial images, yellow, magenta and cyan, are shown in Table 2 below. The inhibitory effect is the regression in colour density (ΔDb, ΔDg,, ΔDr) measured behind a blue, green or red filter, of a recording material containing one of the DIR couplers mentioned in layer 7, compared with that of a recording material which contains no DIR coupler in layer 7, based on the absolute density $\Delta Dn = 1.5$ over the minimum density Dmin. The corresponding quotient of inhibition for the inhibitory values measured behind the green and red filter are also given:

$$Qg = \frac{\Delta Dg}{\Delta Db}\;;\; Qr = \frac{\Delta Dr}{\Delta Db}.$$

After exposure to light through a grey wedge, development was carried out as described in "The British Journal of Photography", 1974, pages 597 and 598.

| Compound No. | Quantity [$10^{-4}$ mol] | Inhibition | | | | |
|---|---|---|---|---|---|---|
| | | ΔDb | ΔDg | Qg | ΔDr | Qr |
| 1 | 2.8 | 11 | 20 | 1.8 | 7 | 0.6 |
| 4 | 1.2 | 12 | 15 | 1.3 | 6 | 0.5 |
| 4 | 1.7 | 16 | 20 | 1.3 | 7 | 0.4 |
| 6 | 1.7 | 3 | 13 | 4.3 | 7 | 2.3 |
| 7 | 1.2 | 5 | 11 | 2.2 | 4 | 0.8 |
| 7 | 1.8 | 7 | 16 | 2.3 | 5 | 0.7 |
| 9 | 1.2 | 11 | 17 | 1.5 | 6 | 0.5 |
| 9 | 1.7 | 11 | 18 | 1.6 | 4 | 0.4 |
| 10 | 1.0 | 8 | 14 | 1.8 | 4 | 0.5 |
| 10 | 1.7 | 9 | 17 | 1.9 | 6 | 0.7 |
| A | 1.2 | 16 | 10 | 0.6 | 0 | 0 |
| A | 2.2 | 20 | 20 | 1.0 | 3 | 0.2 |
| B | 1.3 | 11 | 8 | 0.7 | 0 | 0 |
| B | 1.7 | 20 | 15 | 0.8 | 4 | 0.2 |
| C | 1.4 | 28 | 20 | 0.7 | 7 | 0.3 |
| D | 1.3 | 25 | 18 | 0.7 | 8 | 0.3 |
| D | 1.8 | 35 | 25 | 0.7 | 8 | 0.2 |
| E | 1.8 | 0 | 3 | — | 0 | — |

Table 2 shows that the yellow DIR couplers according to the invention used in the less sensitive blue-sensitive layer produce a considerable inhibition of development in the green-sensitive layers and hence a considerable reduction in gradation of the magenta partial colour image, whereas inhibition in the blue-sensitive layer is comparatively slight. This is expressed in the Qg-valves, which are distinctly above 1. The yellow DIR couplers A, B, C, D, and E used for comparison, on the other hand, have their effect mainly on the gradation of the yellow partial colour image. The yellow DIR couplers according to the invention are also distinctly superior in their effect on the more remotely situated red-sensitive layers.

The colour separation as well as the graininess and sharpness of the material were therefore all considerably improved when the compounds according to the invention were used.

The following are the yellow DIR couplers used for comparison:

TABLE 3

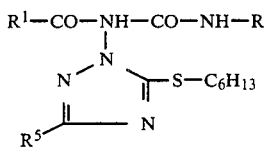

| Compound | $R^1$ | R | $R^5$ |
|---|---|---|---|
| A | t-$C_4H_9$ | 4-Cl, 3-(NH—CO—$(CH_2)_3$—O—(4-t-$C_5H_{11}$-phenyl)) phenyl | H |

= Compound No. 202 of DE-A 2 842 063

| B | 2-$C_{14}H_{29}$-phenyl | 3-$OCH_3$, 4-$SO_2$—NH—$CH_3$ phenyl | —$NH_2$ |
| C | 4-$C_{16}H_{33}$—O-phenyl | 3-$OCH_3$, 4-$SO_2$—N$(CH_3)_2$ phenyl | H |

TABLE 3-continued

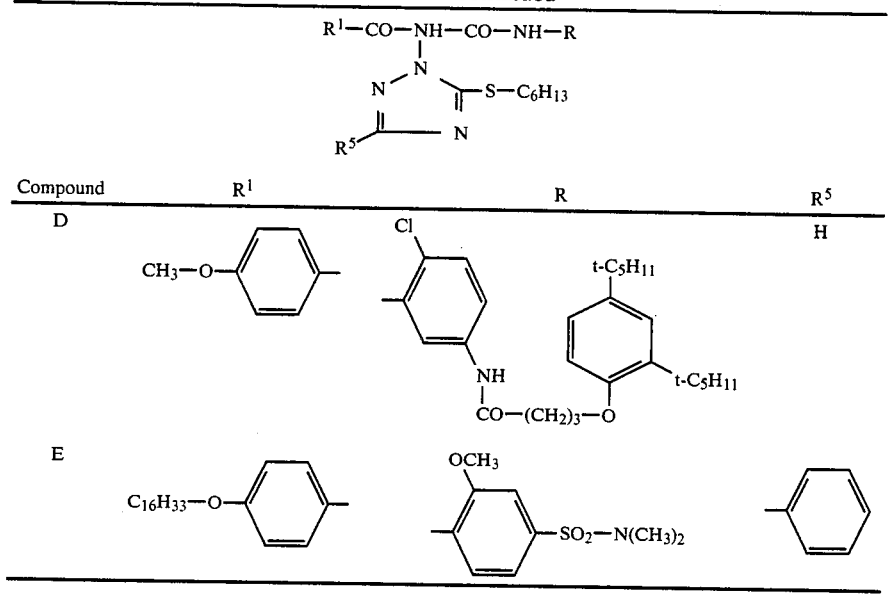

| Compound | R¹ | R | R⁵ |
| --- | --- | --- | --- |
| D | CH₃—O—C₆H₄— | 4-Cl-3-(NHCO(CH₂)₃O-2,4-di-t-C₅H₁₁-C₆H₃)-C₆H₃— | H |
| E | C₁₆H₃₃—O—C₆H₄— | 3-OCH₃-4-CH₃-(SO₂N(CH₃)₂)-C₆H₃— | C₆H₅— |

We claim:

1. A colour photographic recording material having at least one light-sensitive silver halide emulsion layer and, associated with this layer, a DIR coupler which carries, in the coupling position, a yellow coupler attached to a 1,2,4-triazolyl group which can be split off, characterised in that the DIR coupler corresponds to the following formula:

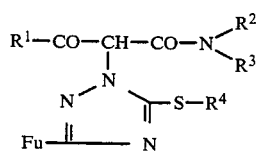

wherein
$R^1$ represents straight-chained or branched alkyl, optionally subtituted aryl or $-NR^5R^6$
$R^2$, $R^5$ represent H or alkyl with 1 to 3 carbon atoms.
$R^3$, $R^6$ represent alkyl with 1 to 18 carbon atoms or optionally substituted aryl.
$R^4$ represents alkyl with 5 to 12 carbon atoms, and
Fu represents an optionally substituted furyl group.

2. A recording material according to claim 1, characterised in that the DIR coupler is contained in a predominantly blue-sensitive silver halide emulsion layer and in that the recording material contains at least one other silver halide emulsion layer, which is predominantly green-sensitive or predominantly red-sensitive.

3. A colour photographic recording material having at least one predominantly blue-sensitive silver halide emulsion layer unit with which at least one yellow coupler is associated, a predominantly green-sensitive silver halide emulsion layer unit with which at least one magenta coupler is associated, and a predominantly red-sensitive silver halide emulsion layer unit with which at least one cyan coupler is associated, characterised in that at least one partial layer of the predominantly blue-sensitive silver halide emulsion layer unit contains a compound corresponding to the following formula:

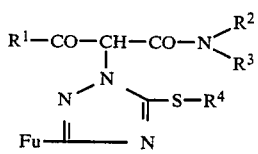

wherein
$R^1$ represents straight-chained or branched alkyl, optionally substituted aryl, or $-NR^5R^6$,
$R^2$, $R^5$ represent H or alkyl with 1 to 3 carbon atoms,
$R^3$, $R^6$ represent alkyl with 1 to 18 carbon atoms, or optionally substituted aryl,
$R^4$ represents alkyl with 5 to 12 carbon atoms, and
Fu represents an optionally substituted furyl group.

* * * * *